US012751625B1

(12) United States Patent
Adams

(10) Patent No.: US 12,751,625 B1
(45) Date of Patent: Oct. 6, 2026

(54) EMBEDDED MARKER SYSTEM AND METHOD FOR SURFACE BIOPSY PROCEDURES AND BENIGN, MALIGNANT AND SUSPICIOUS LESIONS

(71) Applicant: INTRADERM, LLC, Columbia, MD (US)

(72) Inventor: Melanie L. Adams, Columbia, MD (US)

(73) Assignee: INTRADERM, LLC, Columbia, MD (US)

( * ) Notice: Subject to any disclaimer, the term of this patent is extended or adjusted under 35 U.S.C. 154(b) by 361 days.

(21) Appl. No.: 15/041,881

(22) Filed: Feb. 11, 2016

Related U.S. Application Data

(63) Continuation-in-part of application No. 13/852,295, filed on Mar. 28, 2013, now abandoned.

(60) Provisional application No. 61/719,125, filed on Oct. 26, 2012, provisional application No. 61/616,831, filed on Mar. 28, 2012.

(51) Int. Cl.
*A61B 5/00* (2006.01)
*A61B 90/00* (2016.01)

(52) U.S. Cl.
CPC .... *A61B 5/0071* (2013.01); *A61B 2090/3937* (2016.02); *A61B 2090/3987* (2016.02)

(58) Field of Classification Search
CPC ............ A61B 19/54; A61B 2019/5404; A61B 2019/5408; A61B 2019/5437; A61B 2019/545; A61B 2019/5466; A61B 2019/5483; A61K 49/0409; A61K 49/18; A61K 49/222; A61K 49/062; A61K 49/064
See application file for complete search history.

(56) References Cited

U.S. PATENT DOCUMENTS

| | | | | |
|---|---|---|---|---|
| 5,394,886 | A | 3/1995 | Nabai et al. | |
| 6,220,248 | B1 | 4/2001 | Voegele et al. | |
| 6,270,464 | B1 | 8/2001 | Fulton, III et al. | |
| 6,350,244 | B1 | 2/2002 | Fisher | |
| 6,605,047 | B2 | 8/2003 | Zarins et al. | |
| 6,678,398 | B2 | 1/2004 | Wolters et al. | |
| 6,797,521 | B2 | 9/2004 | Grissom et al. | |
| 6,996,433 | B2 | 2/2006 | Burbank et al. | |
| 8,114,006 | B2 | 2/2012 | Cox et al. | |
| 8,135,454 | B2 * | 3/2012 | Daniels | A61B 17/22 600/478 |
| 2005/0234336 | A1 * | 10/2005 | Beckman | A61B 90/39 600/431 |
| 2006/0079770 | A1 | 4/2006 | Sirimanne et al. | |
| 2006/0084865 | A1 | 4/2006 | Burbank et al. | |
| 2006/0224082 | A1 | 10/2006 | Vetter et al. | |
| 2007/0135711 | A1 | 6/2007 | Chernomorsky et al. | |

(Continued)

OTHER PUBLICATIONS

Wiley Periodicals, Inc., By the American Society for Dermatologic Surgery, Inc.; Ultraviolet-Fluorescent Tattoo Location of Cutaneous; Mar. 15, 2012; 5 pages.

(Continued)

*Primary Examiner* — Christopher Koharski
*Assistant Examiner* — Farouk A Bruce
(74) *Attorney, Agent, or Firm* — Schwegman Lundberg & Woessner, P.A.

(57) ABSTRACT

A method of marking the location of a skin biopsy by inserting a marker below the skin surface at or near the biopsy site.

19 Claims, 6 Drawing Sheets

(56) References Cited

U.S. PATENT DOCUMENTS

| | | | |
|---|---|---|---|
| 2007/0299339 A1 | 12/2007 | Chernomorsky et al. | |
| 2009/0088635 A1 | 4/2009 | Fisher | |
| 2009/0088686 A1* | 4/2009 | Cook | A61M 5/427 604/116 |
| 2009/0217840 A1* | 9/2009 | Kundakovic | A61Q 1/02 106/31.03 |
| 2009/0217932 A1* | 9/2009 | Voegele | A61B 5/0084 128/899 |
| 2009/0297441 A1* | 12/2009 | Canham | A61K 49/06 424/9.4 |
| 2010/0234726 A1 | 9/2010 | Sirimanne et al. | |
| 2011/0071431 A1 | 3/2011 | Speeg et al. | |
| 2011/0077512 A1* | 3/2011 | Boswell | A61B 90/39 600/431 |
| 2011/0184280 A1 | 7/2011 | Jones et al. | |
| 2012/0238906 A1 | 9/2012 | Gilchrest et al. | |

OTHER PUBLICATIONS

Wiley Periodicals, Inc., By the American Society for Dermatologic Surgery, Inc.; Rising Concern over Cosmetic Tattoos; Mar. 15, 2012; 6 pages.

American Journal of Roentgenology; Marking the Cavity Site After Stereotactic Core Needle Breast Biopsy; Feb. 2003; 4 pages.

Partnership for Breast Care-Biopsies; Ways to Diagnose the Problem; Mar. 12, 2012; 4 pages.

clinicaltrials.gov; Sonographic Visibility of Breast Biopsy Marker Clips up to 4 Weeks After Placement; Oct. 22, 2007; 3 pages.

Bard Biopsy Systems; UltraClip Dual Trigger; Mar. 12, 212; 2 pages.

* cited by examiner

EMBEDDED MARKER SYSTEM AND METHOD FOR SURFACE BIOPSY PROCEDURES AND BENIGN, MALIGNANT AND SUSPICIOUS LESIONS

CROSS REFERENCE TO RELATED APPLICATION(S)

This application claims priority from U.S. patent application Ser. No. 13/852,295, filed Mar. 28, 2013, U.S. Provisional Patent Application Ser. No. 61/616,831 filed Mar. 28, 2012, and U.S. Provisional Patent Application Ser. No. 61/719,125 filed Oct. 26, 2012 and all of which are incorporated by reference herein.

BACKGROUND OF THE INVENTION

Field of the Invention

The present invention relates to surface biopsies, and more specifically to an embedded marker system and method for skin surface biopsy procedures.

Description of the Related Art

Skin growths may develop into skin cancers, some of the most common being basal cell cancer, squamous cell cancer, and melanoma. Skin cancer is the most common cancer in the United States with over one million people being diagnosed each year. Skin cancer is treatable and curable. Early detection and treatment during the skin growth stage is vital. Skin cancer normally develops in the outer layers of a person's skin, so a tumor can usually be seen, allowing for early detection. Skin cancer may be more commonly diagnosed and treated than any other type of cancer, such as lung, breast, colorectal, and prostate cancer. Skin cancer may be caused by over-exposure to UV rays from the sun or from tanning beds.

Skin cancer symptoms may include changes in the skin that do not heal, ulcering in the skin, discolored skin, and changes in existing moles such as enlargement, or the appearance of jagged edges. Some types of skin cancers include basal cell carcinoma, squamous cell carcinoma, melanoma, and Merkel cell carcinoma. Basal cell carcinoma may appear on sun-exposed skin as a slow growing, flat, firm pale area. The skin area may be small, raised, pink, or red, translucent, shiny, pearly, or waxy, and may bleed after a minor injury. Crusting or bleeding in the center of the tumor may develop, and may be mistaken for a sore that does not heal. Basal cell carcinoma may be the most common skin cancer in humans.

Squamous cell carcinoma may appear as a red, scaling, thickened patch of skin, hard nodules, or dome shaped areas. If untreated, squamous cell carcinoma may develop into a large mass. Melanoma may be brown to black lesions, although they may also be pink, red, or fleshy in color, or they may be signaled by changes in the size, shape, color or elevation of a mole. For example, superficial spreading melanoma may be flat and irregular in shape and color, with different shades of brown. Nodular melanoma may start as a raised area that is dark blackish-blue or bluish-red.

Lentigo maligna melanoma may occur in sun-damaged skin on the face, neck, and arms, and may be large, flat, and tan, with areas of brown. Acral lentiginous melanoma may occur on the palms, soles, or under the nails. Symptoms of melanoma may include asymmetry in color, shape, or other features, or an irregular border. A color change, or the appearance of multiple colors may be an indication of melanoma. A diameter greater than 6 mm, or a continually evolving mole or other skin feature may be an indication of melanoma. Merkel cell carcinoma may be rapidly growing, red, purple, or flesh-toned bumps that may be mistaken for a cyst.

After a skin feature such as a discoloration, mole, or growth, has been identified for further examination, a biopsy (e.g., a physical sample from the skin feature) may be acquired using a scalpel, a punch, or another tool. When skin cancer is suspected, a variety of biopsy techniques may be used to remove part or all of the suspected material. These methods may include: a shave biopsy, a punch biopsy, an incisional biopsy, an excisional biopsy, a curettage biopsy, a fine needle aspirate, and a saucerization biopsy.

A shave biopsy, which may be performed using a small scalpel blade, a curved razor, or a straight razor, may be used to shave a small fragment of a protruding tumor or suspicious tissue, leaving the skin relatively flat after the procedure. A punch biopsy may be performed by using a cylindrical or round knife to take a surface skin sample. Punch biopsies may range from 1 mm to 8 mm. A punch biopsy may permit more accurate measurement of the depth of the site sampled. A potential drawback of a punch biopsy is that the limited sampling may result in incorrect results for a larger lesion. Multiple samples may be taken from the same lesion to provide additional data. An incisional biopsy may be performed using a scalpel, so that a doctor may take a skin sample that is round, elliptical, or long and thin.

An excisional biopsy may remove an entire lesion or tumor. If a lesion is large and/or on the face, a doctor such as a dermatologist and/or patient may prefer to start with one or more small punch biopsies which are capable of healing relatively quickly and with less scarring. The smaller punch biopsy may indicate whether to proceed with a larger excisional biopsy. A curettage biopsy may be taken using a round, cylindrical curette blade. Fine needle aspiration may be performed using a needle tipped syringe that is stabbed into the skin, followed by suction.

A saucerization biopsy may also be known as scoop, scallop, shave excision, or shave excisional biopsy, and may be performed using a single-edged razorblade held in a semicurved position. The saucerization biopsy is similar to a shave biopsy that samples the deeper dermis and potentially subcutaneous fat, which may be obtained by pinching the region of the skin around the lesion and using the curved blade. A potential drawback is that the base of the lesion may be transected and left behind. In addition, saucerization biopsy may result in depressed and/or pigmented scars. Large saucerization biopsies may be sutured.

The biopsy may remove all or part of the skin feature. Between the time the biopsy results have been determined and the time a patient is next seen for treatment, the location where the biopsy was taken may have healed, and the patient and/or the treating physician may not be certain where the biopsy was taken and where further treatment should occur. For example, the biopsied location may appear similar to skin nearby without distinct skin features, or there may be other similar skin features in proximity to where the biopsy was taken. Previously biopsied locations or unrelated scar tissue may appear to be similar to the latest biopsied location, which can cause confusion.

Conventional methods of identifying the location for surface biopsies may include the use of wristbands to identify patients, having patients identify the site in a mirror, digitally photographing the marked site, and examining the site using visual magnification and possibly abrasion. If there is still uncertainty, another biopsy may be performed, and if the second biopsy does not show evidence of a tumor, the surgeon and patient may monitor the suspected location for an additional two years.

One proposed method of identifying the site may involve injection of a visible dye, fluorescent dye, visible tattoo, or the use of a fluorescent tattoo at the location. The fluorescent dye or tattoo may be invisible under ordinary light, but become visible under ultraviolet light (e.g., black lights). Although useful for identification of a location, the permanent appearance of the dye under ultraviolet light in public may be inconvenient and unwanted. In addition, the dye may include natural or synthetic components that may affect the patient's health or appearance over time. Furthermore, the dye may be difficult to remove, and laser or other surgery may cause additional complications during the attempt to remove the dye. Accordingly, a reliable, simple, safe way to identify biopsy locations is needed.

SUMMARY OF THE INVENTION

The present invention relates generally to a method of marking the location of a skin biopsy by inserting a removable and detectable marker below the skin surface at or near the biopsy site. In some embodiments, the marker may be detectable by raising the skin level at or near the biopsy location. The marker may be injected below the biopsy location such that the biopsy location is raised and detectable by feel. The injector may be inserted into the patient's skin at an angle in order to place the marker directly underneath the biopsy location, avoiding having to puncture the biopsy location in order to place the marker. In another embodiment, multiple markers may be placed to mark a biopsy location. In these embodiments, two or more markers may be placed in areas proximate the biopsy location to provide accurate markers in order to accurately identify the biopsy location.

In other embodiments, the markers may not elevate the skin of the patient, but may mark a biopsy location or proximity to a biopsy location in other detectable ways, including providing a harder surface with higher resistance upon being pressed or rubbed.

In other embodiments, the marker may include an injectable degradable dye material which is injected into the patient's skin to provide a color or light variation to mark a biopsy location. The dye marker may only be visible under certain lighting conditions, or other external conditional variations, such as temperature or movement. In preferred embodiments, the dye material may be completely removed from the patient's skin by applying focused heat or energy using a specially formed laser or other mechanism. Additionally, the marker may be completely removed from the patient's skin by excision.

DESCRIPTION OF THE PREFERRED EMBODIMENT(S)

Embodiments of the present invention include a system and method for marking skin biopsy locations on a patient's skin where the markers are unobtrusive to the patient and removable or degradable after use. A preferred embodiment includes a system and method including markers injected partially or fully underneath a patient's skin which produces a slight protrusion of the patient's skin to mark the biopsy location. In accordance with another aspect of a preferred embodiment, there is provided an injector apparatus which is configured to inject markers underneath a patient's skin to produce a slight protrusion to mark the biopsy location.

In a preferred embodiment, there is a method of marking the location of a skin lesion. A patient with a skin growth goes to a physician e.g., a dermatologist (or other licensed medical health professional). The physician may mark a benign or suspicious lesion for a future procedure or for accurate identification for a referring physician. Furthermore, the physician removes the lesion or a portion of it, and marks the site of the lesion with a physical marker embedded partly or preferably fully in the dermis or epidermis of the patient. Alternatively, the physician may mark the site at the time of suture removal or wound check when a diagnosis is reviewed with the patient and there is a need for an additional procedure in the future.

In preferred embodiments, a biopsy marker may be disposed at or in proximity to the biopsy location. In a preferred embodiment, the markers of the system may be injected using devices similar to traditional syringes and needles. In another preferred embodiment, the injection device may include a pen needle configured for one-time use. In another preferred embodiment, the tools used for taking the biopsy sample may be configured to be able to inject the marker into the patient's skin as well. The marker is preferably placed in the dermis, above the subcutaneous tissue, and may be specifically placed into or extend into the reticular dermis or the papillary dermis, and could also be placed into or extend into the epidermis.

In some embodiments, the system and method includes a biocompatible dye which is injected into the patient's skin to mark the biopsy site. The injection of the dye material may result in pigmentation of the patient's skin visible to the medical professional. In some embodiments, the dye material may only become visible upon applying a specific external condition (or factor) such as heat, specific light wavelengths, or movement. In a preferred embodiment, the dye material may be completely removed or degraded by applying focused heat, energy, or other force upon the injected dye material. In another preferred embodiment, the marker may be physically degraded or may be completely removed by excision.

Figure 1A:
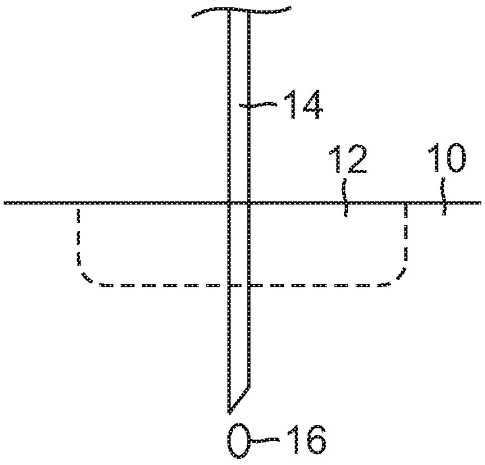
FIGS. 1A and 1B illustrate injection of a marker below a skin surface biopsy location, according to first and second embodiments, respectively.
Figure 1B:
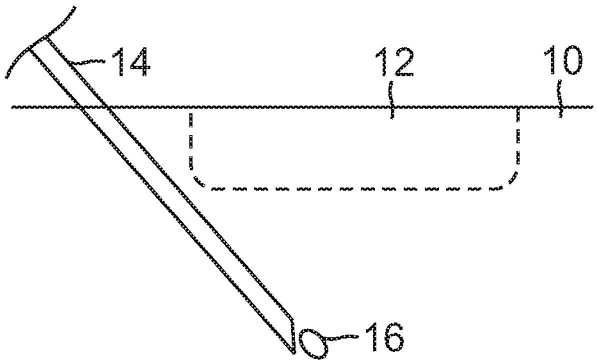

Turning now to the drawings, FIGS. 1A and 1B show a first and a second embodiment of the present invention being used to mark a biopsy location. A marker is placed at or near the biopsy site immediately before, after, or during the biopsy to mark it for future reference. The biopsy location 12 is visible on the surface of the patient's skin 10. According to an embodiment of the present invention, a needle 14 may be inserted into the patient's skin 10 to inject and place a marker 16 at or near the biopsy site 12. The marker may be configured to be sufficiently small to be inserted by a needle which punctures the patient's skin 10 without discomfort. The marker may be made of a non-toxic, durable material such as non-toxic plastic, rubber, metal, composite, or the like. In an alternative embodiment, the marker may be made of a dissolving substance formed into a hard capsule, such as gelatin, carrageenans, cellulose, starch, sugar, saline, corn syrup, or the like, which is configured to dissolve and be absorbed by the patient's body after a predetermined period of time. The marker may be configured to be sufficiently small to be injected into a patient's skin 10, but shaped and sized sufficient to be detectable by feeling through the surface of the patient's skin.

FIG. 1B shows a variation of the embodiment discussed above in FIG. 1A. The needle 14 may be inserted into the patient's skin 10 at an angle sufficient to avoid puncturing the biopsy site 12 which may be undesirable due to sensitivity or in order to ensure accurate biopsy results. The needle 14 may enter the patient's skin at a location adjacent the biopsy site 12. The needle 14 may be inserted at such an angle so as to place the marker 16 directly below the biopsy site 12 for later detection. The marker 16 may be placed underneath the patient's skin, directly below the biopsy site. Alternatively, the marker 16 may be placed proximate the biopsy site at a predetermined distance or angle away from the biopsy site in order to ensure accurate calculation of the biopsy site at a later point.

If the marker 16 location is adjacent to the biopsy site 12, then the location of the biopsy site may be determined from the marker location relative to a patient feature, such as the patient's eyes, nose, mouth, ears, or the top of their head. E.g., the physician might note: "The biopsy site is 0.2 mm in diameter and it is on the patient's left check and is 2.3 cm from the discoloration spot on the tip of the middle of the patient's left alar nasal suculus to the biopsy site, along a line or direction from the tip of the nose passing through the marker, to the center of the biopsy site." The surgeon may then readily determine the location of the biopsy site 12. The patient and/or photo(s) taken by the dermatologist can be used to help confirm the marker 16 location and the biopsy site 12. In a preferred embodiment, the marker is disposed at a depth sufficient to conceal the marker.

Figure 2:
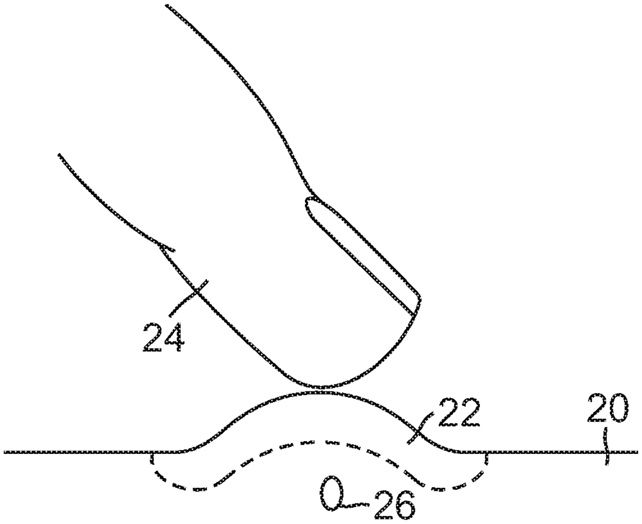
FIG. 2 illustrates an embedded marker below a skin surface, according to a third embodiment.

FIG. 2 shows an illustration of an embodiment of the invention wherein marker 26 is positioned directly underneath biopsy site 22. In a preferred embodiment, marker 26 preferably creates a protrusion 28 in patient's skin 20 such that the patient or examining professional may be able to detect the location of the marker by feeling the surface of the patient's skin 20 with his/her finger 24, or even just by visually examining the surface of skin 20.

Figure 3:
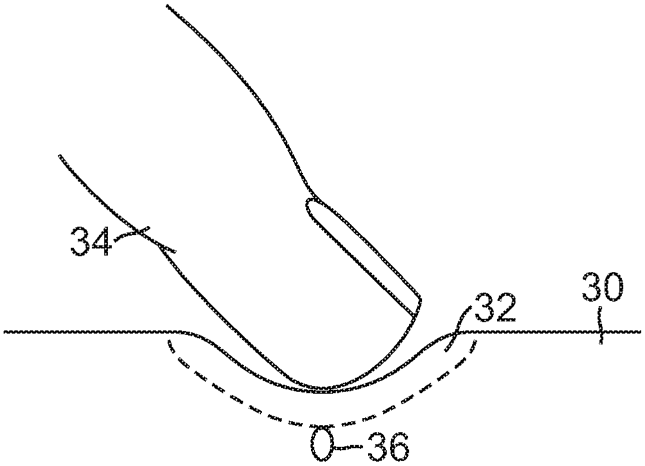
FIG. 3 illustrates an embedded marker below a skin surface, according to a fourth embodiment.

In FIG. 3, an illustration of an alternate embodiment is shown wherein marker 36 configured to be detected by depressing the surface of patient's skin 30 with the patient's or a medical examiner's finger 34. The marker 36 preferably does not create a protrusion on the patient's skin, and is instead detectable by touch because it creates a harder spot on the skin that is more resistant to pressing than other skin locations lacking an embedded marker. The medical examiner would locate marker 36 by palpating skin 30. In an alternate embodiment, the marker may be embedded in the surface of the skin and exposed to the air (not shown) such that a medical examiner may feel the exposed surface of the embedded marker. The marker is injected below the biopsy site 32.

The marker surface may be flush with the user's skin, or it may extend above the surface of the user's skin. In this embodiment, the marker is preferably translucent or flesh toned to blend with the color of the patient's skin. In all embodiments, the marker is preferably sufficiently small so as not to be noticed upon casual observation, but remain detectable under close examination or detection methods described herein.

Figure 4:
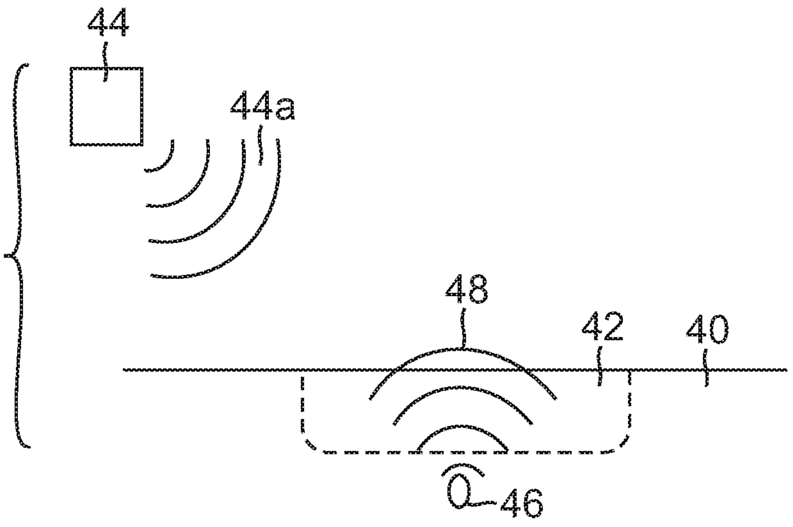
FIG. 4 illustrates an embedded marker below a skin surface and detection thereof using signals according to a fifth embodiment.

FIG. 4 is an illustration of another embodiment of the present invention. In the depicted embodiment, marker 46 is placed in patient's skin 40 underneath or proximate biopsy location 42. Marker 46 may be configured to be responsive to input signals thereby increasing its visibility or detectability to an examiner. In the depicted embodiment, marker 46 is configured with radio frequency identification (RFID) circuitry. Marker 46 may be subjected to a radio frequency signal 44*a* emitted by an RFID interrogator 44. The RFID circuit included in marker 46 may be a passive RFID configuration powered by an active RFID interrogator signal. This Active Reader Passive Tag configuration allows for smaller sized markers 46 and removes the need to include a power source in marker 46 such as a battery. Marker 46 may include an antenna for receiving and transmitting signals and an integrated circuit for storing and processing information, modulating and demodulating a radio frequency signal, collecting direct current power from interrogator signal 44*a*, and other specialized functions.

Marker 46 and interrogator 44 may be configured such that interrogator signal 44*a* activates the RFID circuit in marker 46. In addition, each marker may be uniquely identifiable to permit identification of different biopsy sites or different parts of a biopsy site. The unique identifier may include printed numbers and/or letters, an engraved pattern, a barcode, an RFID signal, or an ultrasound response. In one embodiment, marker 46 may include a small light emitting diode (LED). The LED of marker 46 may be configured to light up when marker 46 is exposed and woken up by RFID interrogator signal 44*a*. The LED may be sufficiently small and low-powered to be operated by the power provided by interrogator signal 44*a* and collected by the marker's antenna and integrated circuit. The medical examiner may locate the biopsy site by exposing patient's skin 40 to an RFID interrogator signal 44*a* using an RFID interrogator. Once interrogator signal 44*a* is sufficiently close to or proximate marker 46 to activate passive RFID integrated circuit contained therein, marker 46 may respond to the signal by lighting up, or otherwise identifying the location to the examiner, as shown by signals 48 representing such radiated signal e.g., light. Alternatively, the marker may create an output signal in response to an x-ray, ultrasound, or other incoming signal.

Alternatively, the marker may be configured to change color in response to a signal to become more visible, such as fluorescing in the presence of ultraviolet light. In these embodiments, the marker may be made of or include a non-toxic material configured to fluoresce when exposed to certain light frequencies, such as ultraviolet "black" light. The marker may include a fluorescing compound or a liquid encapsulated within a capsule composed of non-toxic, durable material. The marker may be embedded at a sufficiently shallow depth in the patient's skin to allow the color of the marker to be seen through the skin. The marker may be configured to be extracted and removed at a later point by a medical expert, or the marker may be configured to be dissolved and/or degraded and absorbed by the patient's body. The marker may be composed of a non-toxic material which dissolves on its own after a predetermined period of time in the patient's body, or configured to degrade when focused heat or energy is applied.

In another embodiment, the marker is preferably magnetic, and may be detected by allowing the patient or medical examiner to detect the marker when another magnet is passed over the patient's skin. The magnet may be magnetically attracted or repelled by a second magnet controlled by the medical examiner, which may cause a protrusion or indentation in the patient's skin such that the biopsy location may be detected.

The marker is preferably made of a material such as plastic, wood, ceramic, metal, or other solid materials. Alternatively, the marker may be a liquid or gel that solidifies after being deposited. In variations of the preferred embodiments, the marker may be composed of a flexible material such as rubber or sponge. In some embodiments, the marker is a soft, fluid filled membrane. In other embodiments, the device may be a composite of several materials, or may include electronics and/or a radio frequency identification (RFID) tag. Preferably, the exterior material of the marker has been approved for injection or other use in the human body, such as in implants, surgery, and/or wound treatment. The marker may be colored, flesh toned, translucent, and/or fluorescent. The marker may include an LED or other light emitter.

In another embodiment, the marker may consist of a specially formed ink, dye, or other substance which is injected into the skin of the patient and results in pigmentation of the patient's skin at the injection site. The marker may be placed in the dermis, above the subcutaneous tissue, and may be specifically placed in or extend into the reticular dermis or the papillary dermis, and could also be placed in or extend into the epidermis. The marker is preferably placed by injection through (or angled so as to pass under) the biopsy site into skin tissue below a surface biopsy location as discussed above in FIGS. 1A, 1B, and 2-4 and below in FIG. 5A or into skin adjacent to the biopsy site, as discussed below in FIG. 5B. The ink or dye is preferably injected in a liquid state, although injection of the marker in a solid, gas or gel-like form is also contemplated.

The pigmentation caused by the ink or dye may be visible under ordinary light to identify biopsy regions. In other embodiments, the pigmentation from the ink or dye may only be visible once placed under a specific light wavelength, such as ultraviolet light (e.g., black lights). In yet other embodiments, the pigmentation marker may become visible when exposed or treated to certain measureable physiological changes, such as light, stimulation by movement or palpation, or temperature.

In an embodiment, the ink or dye may be composed such that the pigmentation caused by the ink or dye may be completely removed from the skin of the patient once the marker is no longer required to identify a biopsy location. For example, after a biopsy has been performed and the biopsy region marked with a dye or ink embodiment of the invention, the patient may return for further treatment which may require identification of the biopsy location. Once the patient has been adequately treated, the pigmentation from the dye or ink marker may be completely erased or removed from the biopsy site to remove unsightly and unneeded bumps or markings on the patient's skin. The removal of the marker may be performed using a laser apparatus or other mechanism configured to remove the injected dye or ink from the patient's skin cells. Such apparatus may be configured to direct a laser, or other focused heat or energy source to a specific area of the patient's skin.

In a particular embodiment, the specially formed ink may be composed of natural, biocompatible pigment encapsulated in synthetic, transparent, biocompatible capsules. The pigment capsule composition may be such that when exposed to a specially formed laser or other mechanism configured to apply focused heat or other energy to a specific area of skin, the capsules break apart releasing the natural pigment contained there within. The natural pigment may then be absorbed and/or disposed of by the patient's body, resulting in erasure or removal of the identifying marker from the patient's skin.

Figure 5A:
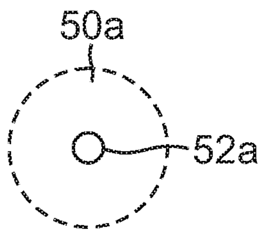
FIGS. 5A and 5B illustrate disposition of one or more markers relative to a biopsy location according to sixth and seventh embodiments, respectively.
Figure 5B:
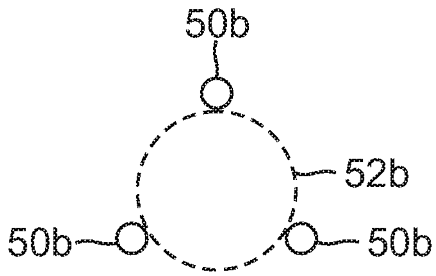

The ink or dye pigmentation used in these embodiments, as well as the removal process and apparatus therefor, may have additional uses and applications, even outside of the medical field. These uses and applications may include: textiles and fabrics; paper and paper goods; leather; wood; natural or synthetic dyes related to food; petroleum-based products and applications such as waxes, oils, polishes, gasoline; dyes or stains for biological applications such as fur, hair, skin; photographic emulsions and color photographs; plastics, resins, and rubber products; toys, games, and stickers; temporary tattoos; makeup and cosmetics related tattoos or skin dyes; glow in the dark powder; permanent makeup; temporary makeup; medical makeup; tie dye; beard and hair dye; dyeing and finishing garments and apparel; woven fabric dyeing and finishing; human hair wigs; canvas bags; purses and luxury items; yarn; cosmetic and medical skin dyeing and tanning; spray paint; mulch dye color; concrete dye and pigmentation; fabric shoe dye; leather shoe dye; pharmaceuticals; suture stains and dyes; staining of medical instruments and accessories; paint; art supplies, markers, pens, and other stationary FIGS. 5A and 5B are illustrations of two embodiments of methods of marking a biopsy site according to the present invention. FIG. 5A is a top down view of a biopsy site 50*a* of a patient's skin. In this embodiment, marker 52*a* is inserted in the patient's skin directly underneath biopsy site 50*a*. Biopsy site 50*a* may be located upon examination and detection of marker 52*a* by a medical examiner using any of the detection methods according to the present invention.

FIG. 5B shows a top down view of a biopsy site 50*b* of a patient's skin with three markers 50*b* demarcating boundaries of the biopsy site. In this embodiment, three markers 50*b* are placed in the patient's skin proximate the boundary of the biopsy site equidistant from each other to aid in determining biopsy site 50*a*. In this case, the physician's notes to the surgeon could state, e.g., "The biopsy site is at the center of three markers." The notes may also indicate where, in relation to a landmark, the markers are, e.g., "The markers are approximately 2.1 cm substantially directly below the bottom of the patient's right ear lobe."

FIG. 5B shows a biopsy site with a circular shape for this discussion however biopsy sites may include a variety of different shapes, formations and sizes. It will be understood that in this embodiment, any number of two or more markers 50*b* may be used to demarcate the boundaries or locations of the biopsy on a patient's skin. Such multiple markers may be used to indicate the borders of an elongated and/or irregularly shaped skin lesion or biopsy site.

Figure 6:
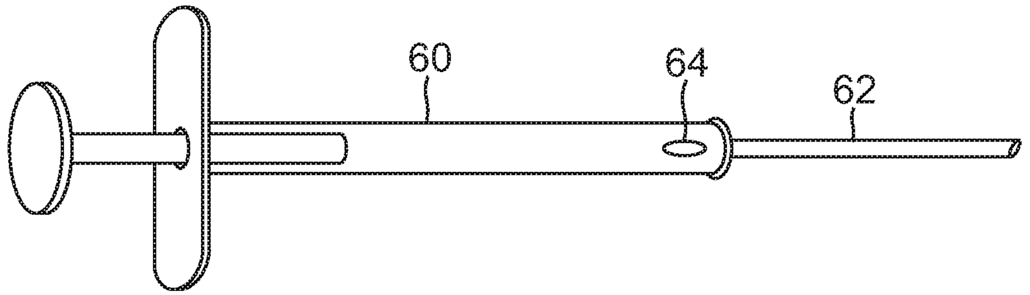
FIGS. 6 and 7 illustrate injector devices, according to eighth and ninth embodiments, respectively.

FIG. 6 is an illustration showing a syringe 60 and needle 62 combination that may be used to deliver a marker 64 below a skin surface, according to multiple embodiments. The syringe 60 and needle 62 combination may be configured to accurately position and place a marker 64 underneath a patient's skin. The syringe 60 and needle 62 may be configured similar to traditional syringe and needle combinations which are used to deliver or extract fluids in medical uses, except that in the embodiments contemplated by the present invention, the syringe and needle combination may be sufficiently sized and shaped to load and deliver marker 64 in accordance with the embodiments as disclosed herein.

The syringe 60 and needle 62 combination may be prepackaged with a marker 64 loaded into the syringe portion 60 ready to be injected into a patient. In another embodiment, the syringe 60 and needle 62 combination may need to be loaded with a marker by a medical professional. The syringe 60 and/or needle 62 combination may be for one time use or may be sterilized and reloaded with another marker for repeated use. An inert fluid such as a saline solution may be included in the syringe portion to aid in delivering the marker 64 through the needle 64 and into the patient's skin.

Figure 7:
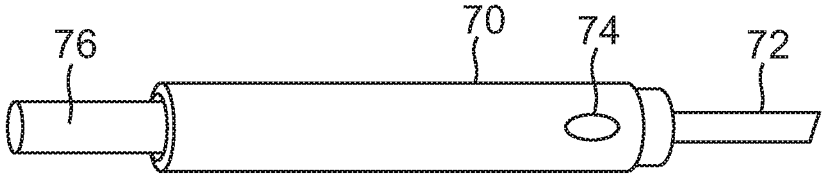

FIG. 7 is an illustration of an injector device 70 according to an embodiment. The injector device 70 may be spring loaded and have a retracted needle tip 72. The injector tip may be pressed against a user's skin and triggered with a push button 76 to inject marker 74 into a person's skin below or adjacent to a skin surface biopsy location. Injector device 70 may be preloaded with a marker 74 of the present invention and injector device 70 may be configured to be discarded after a single use.

Figure 8:
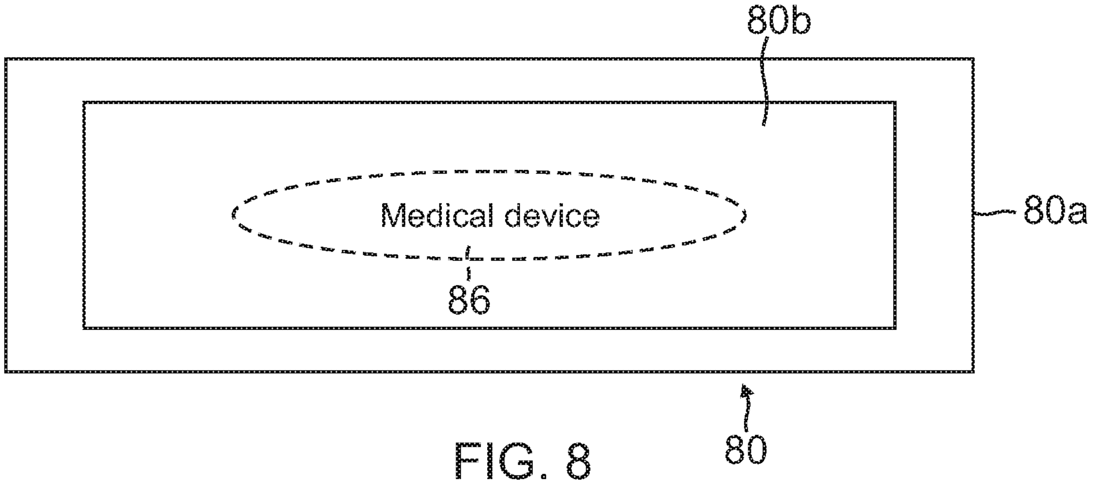
FIG. 8 illustrates disposable, sterile packaging for an injection device, according to a tenth embodiment.

FIG. 8 illustrates disposable packaging for an injection device according to an embodiment. Packaging 80 may be a plastic envelope as is typical in the medical field. It may have a transparent or translucent panel 80*b* to permit examination of the injection device, and may have an area at end 80*a* that is for tearing open. The marker device is represented by medical device 86. The step of placing the marker at or proximate the biopsy site may be done before, during or after the healing of the skin at the biopsy site.

Further Embodiment(S)

Since the dermis contains vessels that lead to the body's blood stream, it is ideal that the agents (colorant in our case) selected to mark the skin do not penetrate past the epidermis layer. Also, since skin sheds over time, the colorant must penetrate the top of the epidermis layer to have some degree of permanence (long enough until the patient can receive a follow-up treatment). The colorants should not go beyond the skin layer (i.e., should not go into the dermis) so as not to enter the blood stream.

The ink or dye may be composed of natural, biocompatible pigment may be an already FDA approved substance. Various natural dyes may be used. Various synthetic dyes may be used as well.

Figure 9:
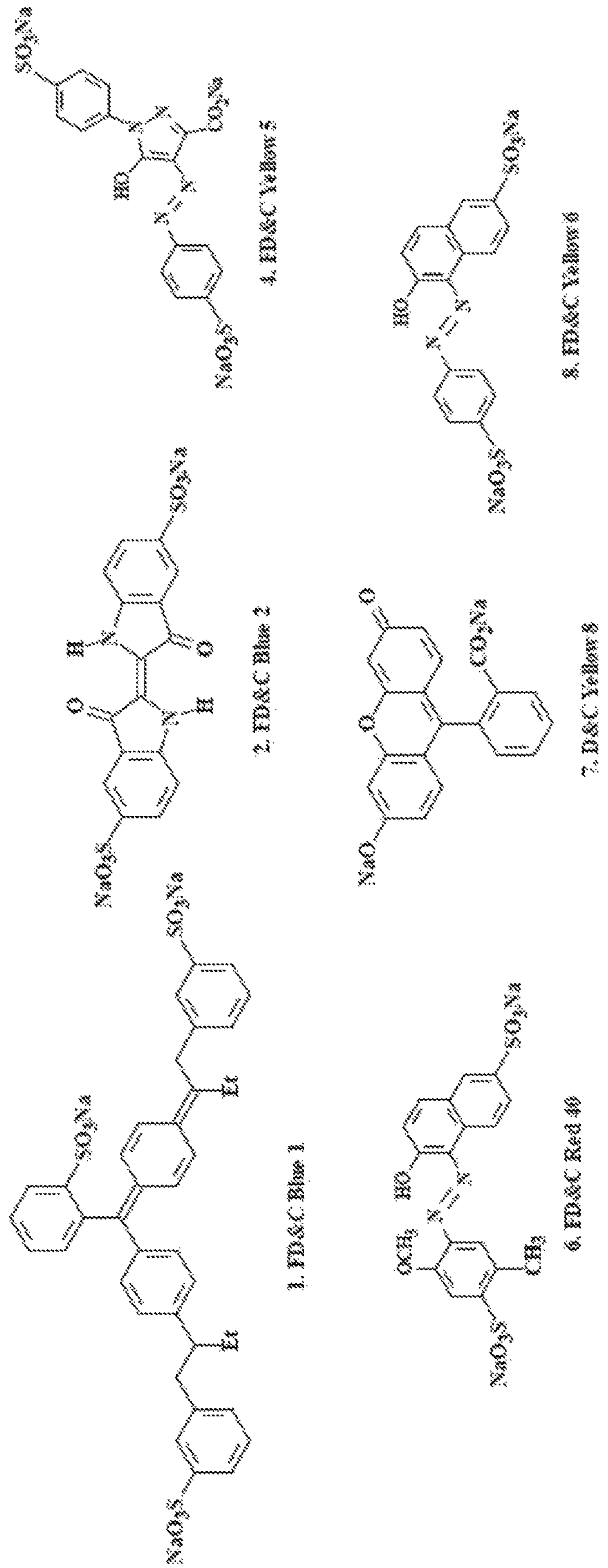
FIGS. 9 and 10 illustrate chemical diagrams of various dyes.
Figure 10:
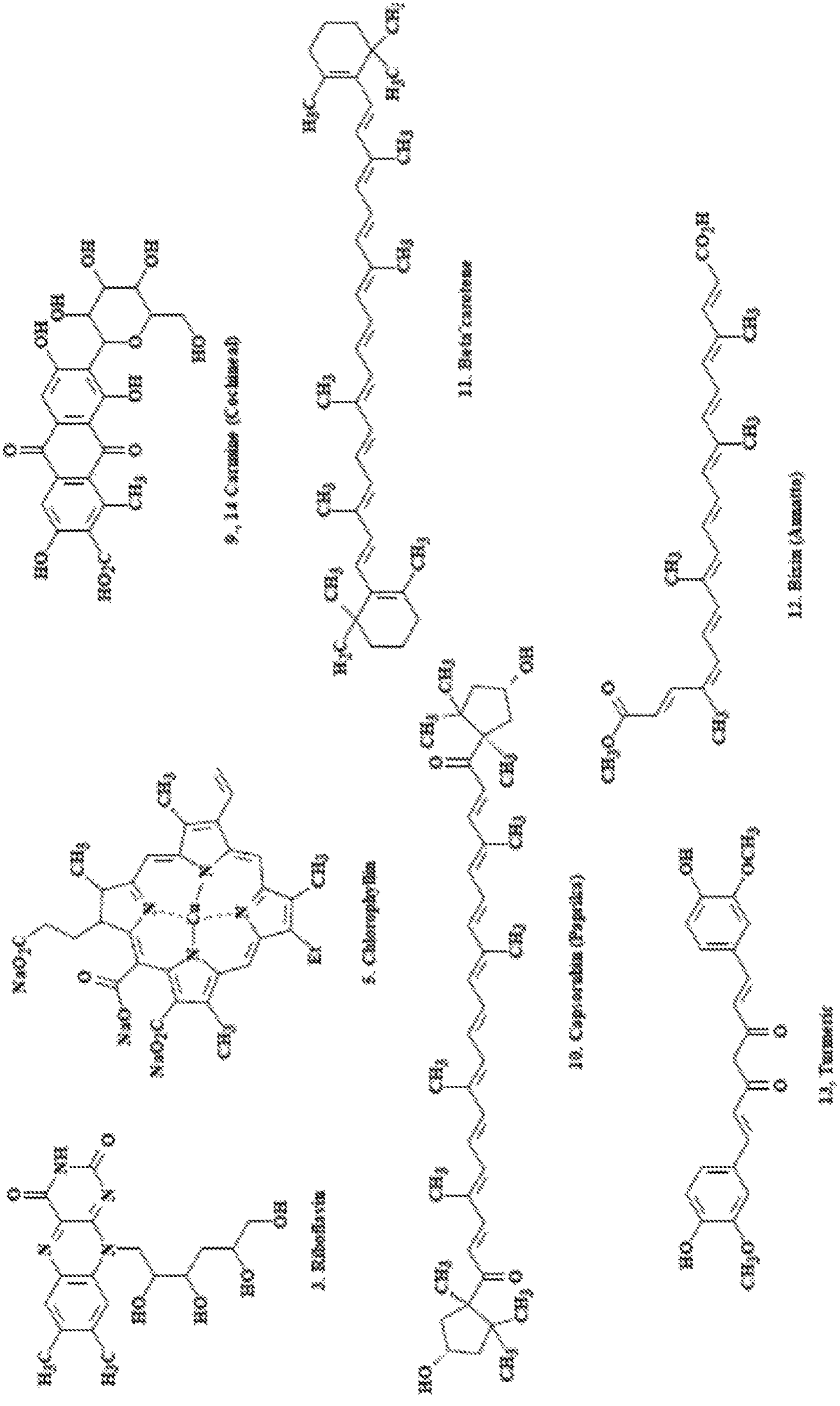

The dye is injected so as to penetrate into and remain in the epidermis layer of human skin, at least in an amount sufficient to observe the dye and for at least 30 days and preferably at least 60 days, at least in an amount sufficient to observe the dye. Preferably the dye would be absorbed and/or disappear or substantially disappear after about three months or more preferably six months or about six months. The below are Certifiable U.S. Colorants. Chemical diagrams are shown in FIGS. 9 and 10.

Synthetic Dyes

| Dye No. | FD&C or D&C No. | Name | FW | Active Dye (%) |
|---|---|---|---|---|
| 1 | Blue 1 | Erioglaucine sodium salt | 792 | Unspecified |
| 2 | Blue 2 | Indigo Carmine | 466 | 98 |
| 4 | Yellow 5 | Tartrazine | 534 | Unspecified |
| 6 | Red 40 | Allura | 496 | Unspecified |
| 7 | Yellow 8 | Fluorescein | 332 | Unspecified |
| 8 | Yellow 6 | Sunset Yellow FCF | 452 | Unspecified |

Natural Dyes

| Dye No. | Common Name | Source | FW | Active Dye (%) |
|---|---|---|---|---|
| 3 | Riboflavin | Vitamin B2 | 376.36 | 98 |
| 5 | Chlorophyllin sodium salt | Chlorophyllin | 724.15 | Unspecified |
| 9 | Carmine | Cochineal extract | 492.39 | 3.5 |
| 10 | Paprika | | 1185.78* | Unspecified |
| 11 | Beta-carotene | Carrots | 536.87 | Unspecified |
| 12 | Annato | Annato seeds | 380.48 | Unspecified |
| 13 | Turmeric | Root extract | 368.38 | 8.5 |
| 14 | Acid Proof Cochineal | Cochineal extract | 492.39** | 7.5 |

For injection, the pH should be 7 or approximately 7, except that fluorescein may be about pH 9.

An injection protocol includes as above, modified to the extent that, e.g., 1 ml of dye in a liquid form is injected into the epidermis.

The solvent for the dye may include any of the following eluents (for example in the proportions but other proportions may be used):

1. Chloroform-acetic acid=9:1
2. Toluene-acetic acid=6.5:3.5
3. Ethyl acetate-pyridine-water=6:3:1
4. Acetone-water=7:3
5. Propanol-ammonia=1:1
6. Butanol-pyridine-water=4:2:1
7. Propanol-acetic acid-water=10:3:3
8. Hexane-ethyl acetate=4:1

Dye: Concentration and solvents

| Dye | Dye Name | Amount of Dye, pH | Dye | Dye Name | Amount of Dye |
|---|---|---|---|---|---|
| 1 | FD&C Blue 1 | 1 mL of 2.00% water solution, pH~7 | 8 | FD & C Yellow 6 | 1 mL of 1.00% ethanol solution |
| 2 | FD&C Blue 2 | 1 mL of 2.00% water solution, PH~7 | 9 | Carmine | 1 mL of 10.00% of stock solution in 50.00% ethanol |
| 3 | Riboflavin | 1 mL of 0.25% water solution, pH~9 | 10 | Paprika | 1 mL of 10.00% of stock solution in ethanol |

-continued

| Dye: Concentration and solvents | | | | | |
|---|---|---|---|---|---|
| Dye | Dye Name | Amount of Dye, pH | Dye | Dye Name | Amount of Dye |
| 4 | FD&C Yellow 5 | 1 mL of 2.00% water solution, pH~7 | 11 | Beta carotene | 1 mL of stock solution in DMF |
| 5 | Chlorophyllin Sodium Copper salt | 1 mL of 2.00% water solution, pH~7 | 12 | Annatto | 1 mL of 10.00% of stock solution in 50.00% ethanol |
| 6 | FD&C Red 40 | 1 mL of 2.00% water solution, pH~7 | 13 | Turmeric | 1 mL of 10.00% of stock solution in 50.00% ethanol |
| 7 | | Fluorescein | | 1 mL of | 0.25% water solution, pH~9 |

| Dye: Concentration and solvents | | | |
|---|---|---|---|
| Dye | Dye Name | Concentration % | Solvent |
| 1 | FD&C Blue 1 | 0.1 | EtOH, DMF, 2-metoxyethanol, benzyl alcohol |
| 2 | FD&C Blue 2 | 0.1 | DMF, 2-metoxyethanol |
| 3 | Riboflavin | 0.05 | EtOH, DMF, 2-metoxyethanol, benzyl alcohol |
| 5 | Chlorophyllin Sodium Copper Salt | 0.1 | EtOH, DMF, 2-metoxyethanol, benzyl alcohol |
| 7 | Fluorescein | 0.05 | EtOH, DMF, 2-metoxyethanol, benzyl alcohol |
| 10 | Paprika solution | 1% of stock | DMF, 2-metoxyethanol, Ligroin |
| | Beta Carotene | 1% of stock solution | EtOH, DMF, 2-metoxyethanol |
| | Annatto | 1% of stock solution | EtOH, DMF, 2-metoxyethanol, |

Dyes 3 and 7 could be fluorescent.

Although the invention has been described using specific terms, devices, and/or methods, such description is for illustrative purposes of the preferred embodiment(s) only. Changes may be made to the preferred embodiment(s) by those of ordinary skill in the art without departing from the scope of the present invention, which is set forth in the following claims. In addition, it should be understood that aspects of the preferred embodiment(s) generally may be interchanged in whole or in part.

What is claimed is:

1. A method for identifying a skin biopsy site of a patient having skin cancer, the method comprising:

acquiring a biopsy sample of a skin surface feature at the skin biopsy site of the patient;

determining skin cancer is present at the skin biopsy site, wherein the biopsy sample is used to determine skin cancer is present at the skin biopsy site;

injecting a temporary, liquid dye into the dermis layer of the skin of the patient that is at or proximate to the skin biopsy site after determining skin cancer is present at the biopsy site; and wherein the temporary liquid dye is visible for one day to six months.

2. The method of claim 1, wherein the amount of dye is 1 ml.

3. The method of claim 1, further comprising removing the temporary, liquid dye from the skin.

4. The method of claim 1, wherein the dye comprises a material capable of pigmenting the skin of the patient.

5. The method of claim 4, wherein the skin pigmentation caused by the dye is degradable by application of energy.

6. The method of claim 1, wherein the temporary, liquid dye is injected proximate to the skin biopsy site.

7. The method of claim 1, wherein the temporary, liquid dye is injected into the dermis layer of the skin of the patient at the skin biopsy site.

8. The method of claim 1, wherein injecting the temporary, liquid dye into the dermis layer of the skin of the patient that is at or proximate to the skin biopsy site after determining skin cancer is present at the biopsy site, includes:

marking a subsection of the biopsy site.

9. The method of claim 8, wherein injecting the temporary, liquid dye into the dermis layer of the skin of the patient that is at or proximate to the skin biopsy site after determining skin cancer is present at the biopsy site, includes:

refraining from marking a portion of the biopsy site outside of a subsection of the biopsy site.

10. The method of claim 1, wherein determination that skin cancer is present at the skin biopsy site is made only after the biopsy sample is acquired.

11. A method for identifying a skin biopsy site of a patient having skin cancer, the method comprising:

acquiring a biopsy sample of a skin surface feature at the skin biopsy site of the patient;

determining skin cancer is present in the biopsy sample from the skin surface feature at the skin biopsy site;

injecting a temporary, liquid dye into the dermis layer of the skin of the patient that is at or proximate to the skin biopsy site after determining skin cancer is present at the biopsy site;

refraining from injecting the temporary liquid dye into the dermis layer of the skin remote from the skin biopsy site after determining skin cancer is present at the biopsy site; and observing the skin biopsy site having the liquid dye at or proximate to the biopsy site, at least one day after acquiring the biopsy sample.

12. The method of claim 11, wherein the liquid dye includes one or more of erioglaucine sodium salt, indigo carmine, tartrazine, chlorophyllin sodium salt, allura, paprika, beta-carotene, annatto.

13. The method of claim 11, wherein:

a first healthcare provider injects the temporary, liquid dye into the dermis layer of the skin of the patient; and a second healthcare provider observes the skin biopsy site having the liquid dye at or proximate to the biopsy site.

14. The method of claim 13, further comprising transmitting information from the first healthcare provider to the second healthcare provider, the information related to a location of the temporary, liquid dye with respect to the patient.

15. The method of claim 11, wherein the injecting a temporary, liquid dye into the dermis layer of the skin of the patient includes locating the temporary, liquid dye directly below the skin biopsy site.

16. The method of claim 15, further comprising puncturing the skin outside of the skin biopsy site.

17. The method of claim 11, wherein injecting the temporary, liquid dye into the dermis layer of the skin of the patient that is at or proximate to the skin biopsy site after determining skin cancer is present at the biopsy site, includes:

marking a subsection of the biopsy site.

18. The method of claim 17, wherein injecting the temporary, liquid dye into the dermis layer of the skin of the patient that is at or proximate to the skin biopsy site after determining skin cancer is present at the biopsy site, includes:

refraining from marking a portion of the biopsy site outside of a subsection of the biopsy site.

19. The method of claim 11, wherein determination that skin cancer is present at the skin biopsy site is made only after the biopsy sample is acquired.

* * * * *